United States Patent [19]

Belmont

[11] Patent Number: 5,741,938
[45] Date of Patent: Apr. 21, 1998

[54] PRODUCTION OF ALKYL ARALKYL KEONES FROM ALLYLIC-ARALKENYL SECONDARY ALCOHOLS

[75] Inventor: Stephen E. Belmont, Baton Rouge, La.

[73] Assignee: Albemarle Corporation, Richmond, Va.

[21] Appl. No.: 804,528

[22] Filed: Feb. 21, 1997

[51] Int. Cl.$^6$ .................................................... C07C 45/51
[52] U.S. Cl. ............................................................ 568/322
[58] Field of Search ............................................... 568/322

[56] References Cited

U.S. PATENT DOCUMENTS

| | | | |
|---|---|---|---|
| 4,420,639 | 12/1983 | Lake et al. | 568/328 |
| 5,101,077 | 3/1992 | Drent | 568/322 |
| 5,225,603 | 7/1993 | Aslam et al. | 568/315 |

OTHER PUBLICATIONS

Mohammad Aslam et al., "Convenient Syntheses of Nabumetone" Communications, Nov. 1989, pp. 869–870.

Bingham et al., "Homogeneous Catlysis of Olefin Isomerisation. Part VI. Pent–1–ene Isomerisation catalysed by Solutions of Dodecacarbonyltri–iron(o) and of Bis(benzonitrile)dichloropalladium(II)in Benzene" J Chem Soc. Dalton Trans, 1974, pp. 1521–1524.

Melpolder and Heck, "A Palladiium–Catalyzed Arylation of Allylic Alcohols with Aryl Halides", J. Org. Chem. 1976, vol. 41, pp. 265 265–272.

*Primary Examiner*—James H. Reamer
*Attorney, Agent, or Firm*—Philip M. Pippenger

[57] ABSTRACT

The process forms an alkyl aralkyl ketone from an aralkenyl secondary alcohol having an allylic double bond relative to the hydroxycarbinyl group, and having the allylic double bond positioned between the aryl moiety and the hydroxycarbinyl group. This is accomplished by heating the alcohol in a chemically indifferent organic liquid medium to which a catalytic quantity of an iron polycarbonyl has been added, so that an internal rearrangement occurs. Among the ketones that can be efficiently produced in this manner is nonsteroidal antiinflammatory agent, 4-(6'-methoxy-2'-naphthyl)-butan-2-one, generally known as nabumetone.

19 Claims, No Drawings

5,741,938

1

PRODUCTION OF ALKYL ARALKYL KEONES FROM ALLYLIC-ARALKENYL SECONDARY ALCOHOLS

TECHNICAL FIELD

This invention relates to processes for the synthesis of alkyl aralkyl ketones, especially nabumetone or its analogs, by selective intramolecular transfer of hydrogen in allylic-aralkenyl secondary alcohols.

BACKGROUND

Alkyl aralkyl ketones are useful both as intermediates and in many cases as pharmaceutical agents. For example, U.S. Pat. No. 4,420,639 describes, inter alia, a class of alkyl aralkyl ketones in which the aryl portion of the aralkyl group is a 2-naphthyl group having a specified substituent in the 6-position. These compounds are reported to have antiinflammatory and/or analgesic activity, and to have the additional advantage of not excessively irritating the stomach at the therapeutic dose. Among the compounds described in U.S. Pat. No. 4,420,639 is the well known non-steroidal antiinflammatory agent, 4-(6'-methoxy-2'-naphthyl)-butan-2-one, generally known as nabumetone.

While analogous compounds having a double bond in the alkyl chain of the aralkyl group are also reported to possess the same beneficial properties, it is further reported in the patent that the carbon-carbon double bond tends to impart a degree of oestrogenicity to these compounds. For this reason, the patent recommends using compounds which do not contain the carbon-carbon double bond.

It has been reported (Melpolder, J. B. and Heck, R. F., *J. Org. Chem.* 1976, 41, 265) that palladium-catalyzed arylation of allylic alcohols with aromatic halides yields mixtures of alkyl aralkyl ketones and of aralkenyl secondary alcohols having an allylic double bond relative to the hydroxycarbinyl group. In view of the presence of the allylic carbon-carbon double bond in the secondary alcohol it would be desirable to provide an efficacious way of converting the secondary alcohol into a corresponding alkyl aryl ketone.

SUMMARY OF THE INVENTION

This invention provides an efficacious process for forming an alkyl aralkyl ketone from an aralkenyl secondary alcohol having an allylic double bond relative to the hydroxycarbinyl group, and having the allylic double bond disposed between the aryl moiety and the hydroxycarbinyl group. This rearrangement is effected by heating the aralkenyl secondary alcohol in a suitably inert organic liquid medium to which a catalytic quantity of an iron polycarbonyl has been added. A preferred example of this rearrangement is the conversion of 4-(6'-methoxy-2'-naphthyl)-but-3-en-2-ol to 4-(6'-methoxy-2'-naphthyl)-butan-2-one.

Thus in accordance with one embodiment of this invention there is provided a process which comprises heating a mixture formed at least from (i) one or more aralkenyl secondary alcohols having an allylic double bond relative to the hydroxycarbinyl group, and having the allylic double bond disposed between the aryl moiety and the hydroxycarbinyl group, and (ii) at least one iron polycarbonyl. The process is conducted in the liquid phase, typically in an ancillary organic solvent or diluent, and under conditions that produce alkyl aralkyl ketones having the same skeletal configuration but without the double bond. It is to be understood that by "the same skeletal configuration" is meant only that the carbon atom to which the hydroxyl group is attached becomes the carbon atom of the keto (carbonyl) group.

In this embodiment oftentimes the initial mixture comprises in addition to at least one such allylic aralkenyl secondary alcohol, a quantity of the alkyl aralkyl ketone to be produced. For example the initial mixture may contain substantial proportions of each of 4-aryl-but-3-en-2-ol and 4-aryl-butan-2-one, or of each of 5-aryl-pent-4-en-3-ol and 5-arylpentan-3-one, or of each of 4-aryl-pent-3-en-2-ol and 4-aryl-pentan-2-one, etc.

Besides making possible conversion of various aralkenyl secondary alcohols of the appropriate structure into the corresponding alkyl aralkyl ketones, this invention additionally makes possible a new two-step synthetic route for the preparation of nabumetone and other analogous compounds reported for example in U.S. Pat. No. 4,420,639. In this embodiment the process comprises (a) forming allylic secondary arylalkenol by palladium-catalyzed arylation of an allylic secondary alkenol with an aryl halide (chloride, bromide, or iodide, preferably bromide), and (b) heating a liquid phase mixture formed from at least the following ingredients or components: (i) at least a portion of the allylic secondary alkenol formed in (a) and (ii) at least one iron polycarbonyl, such that alkyl aralkyl ketone is produced having the same skeletal configuration as the aralkenol but without the double bond. Typically the palladium-catalyzed arylation in (a) produces a mixture of allylic secondary arylalkenol and alkyl aralkyl ketone having the same skeletal configuration as the aralkenol but without the double bond, and thus in a preferred embodiment, step (b) is conducted using the reaction mixture formed in (a) without isolation of the desired product and, most preferably, in the same reaction vessel, simply by addition of the iron polycarbonyl to the reaction product mixture formed in (a) and heating to the desired reaction temperature(s). The addition of the iron polycarbonyl to the reaction product mixture formed in (a) and the heating in (b) may be conducted concurrently, and/or sequentially in any order.

These and other embodiments and features of the invention will become still further apparent from the ensuing description.

FURTHER DETAILED DESCRIPTION

Firstly, the process for converting allylic aralkenyl secondary alcohols to alkyl aralkyl ketone of the same skeletal configuration will be discussed. For convenience this process will sometimes be referred to hereinafter as the transformation process.

Aralkenyl secondary alcohols suitable for use in the transformation process of this invention may be depicted by the formula:

$$R-Z \quad \quad (I)$$

where R is an aryl group; and Z is a hydroxy-substituted alkenyl group having in the range of 4 to about 18 carbon atoms having the hydroxyl substituent on an internal carbon atom more remote from R than the double bond, and with the double bond allylic with respect to the internal carbon atom having the hydroxyl substituent. Preferably, but not necessarily, the hydroxyl group is substituted on the third carbon atom from the aryl group.

Particularly preferred allylic aralkenyl secondary alcohols for use in the transformation process are those depicted by the formula

(II)

where each of $R^1$ and $R^2$ is, independently, a hydrogen atom, or an alkyl group containing 1 to 3 carbon atoms; $R^3$ is a hydrogen atom or a methyl group; $R^4$ is an alkyl group containing 1 to 4 carbon atoms; and Ar is a 2-naphthyl group preferably having a substituent in the 6-position. Such substituent can be, for example, a chlorine atom, a bromine atom, a methoxy group, a methylthio group, and a straight or branched chain alkyl group having 1 to 4 carbon atoms. Most preferably this substituent is a methoxy group.

Iron polycarbonyls suitable as candidates for use as catalysts in the transformation process include, for example, $Fe(CO)_5$, $Fe(CO)_4$, $Fe_2(CO)_9$, $Fe_3(CO)_{12}$, $Fe(CO)_4H_2$, $Fe(CO)_4Hg$, $Fe(CO)_2(NO)_2$, and butadiene iron tricarbonyl. Of these iron polycarbonyls, $Fe(CO)_5$ and $Fe_3(CO)_{12}$ are preferred.

The transformation process can be conducted in any appropriate liquid organic solvent which does not materially interfere with the transformation reaction. Thus use may be made of such solvents as liquid paraffinic, cycloparaffinic and/or aromatic hydrocarbons; liquid paraffinic, cycloparaffinic and/or aromatic liquid halohydrocarbons; liquid fluorocarbons, liquid ethers, liquid nitriles, and other similar solvents.

To effect the transformation process a mixture is formed from (a) the aralkenyl secondary alcohol, (b) an effective catalytic quantity of the iron polycarbonyl catalyst, and usually and preferably (c) a suitable liquid organic solvent. Such mixture is heated at one or more temperatures in the range of about 20° to about 200° C., and preferably in the range of about 60 and about 100° C., for a period of time at least sufficient to achieve transformation of at least a portion of the alcohol to the corresponding ketone. Catalytic amounts of the iron polycarbonyl catalyst typically fall in the range of about 0.01 to about 0.20 mole of iron as iron polycarbonyl per mole of the aralkenyl secondary alcohol used sufficient to achieve good conversions of the alcohol to the ketone. It is desirable to ensure that the mixture is well-mixed or agitated during at least a substantial portion (e.g., at least half of the total time) of the transformation process.

The alcohol product formed in the process can be recovered if desired by conventional techniques such as column chromatography, distillation, or the like.

The two-stage process embodiments of this invention will now be considered.

In the first stage the above allylic aralkenyl secondary alcohol is produced by the palladium-catalyzed arylation of an allylic alcohol with an aromatic halide. The second stage involves converting the allylic aralkenyl secondary alcohol, or at least a portion thereof, to the corresponding alkyl aralkyl ketone using the transformation process described above.

To perform the first stage, the best known way is to form a reaction mixture from an aryl halide reactant (preferably a chloride or bromide), the allylic secondary alkenol reactant, one or more liquid polar organic solvent/diluents, one or more secondary or tertiary amines to serve as halogen halide acceptor(s), and a palladium catalyst system.

Virtually any aryl halide can be used in the reaction provided it is free of one or more substituents that would prevent or materially inhibit the desired reaction. Thus typically the aryl halide used will depend upon the particular alkyl aralkyl ketone to be produced in the second stage transformation process. Thus to produce the preferred secondary alcohols of Formula (II) above for use in the transformation process, the aryl halide preferably will be 2-bromonaphthalene preferably having a pharmacologically acceptable substituent in the 6-position of the type described above in respect of Formula (II).

The secondary alkenol used as the co-reactant in the first stage likewise can vary widely as long as it has the requisite allylic double bond and is free of one or more substituents that would prevent or materially inhibit the desired reaction. Thus to produce the preferred secondary alcohols of Formula (II) above for rise in the transformation process, use will be made of a secondary alkenol of the formula

(III)

where each of $R^1$, $R^2$, $R^3$, and $R^4$ is as described above in respect of Formula (II).

Examples of suitable solvent/diluents preferably used in the arylation reaction include tetrahydrofuran, 1,4-dioxane, diglyme, triglyme, acetonitrile, propionitrile, benzonitrile, N,N-dimethylformamide, N,N-dimethylacetamide, dimethylsulfoxide, nitrobenzene, sulfolane, acetone, butanone and cyclohexanone. Preferred solvent/diluents are one or more aprotic solvents each having a dielectric constant of at least about 10 (especially 10 to 30) at a temperature in the range of 20° to 25° C. From the cost-effectiveness standpoint, hydrocarbyl ketones with 4 or more carbon atoms in the molecule (e.g., 4 to about 8) are especially preferable. Examples include diethyl ketone, methyl isobutyl ketone, 2-pentanone, 2-hexanone, 2-heptanone, 3-heptanone, 4-heptanone, and like liquid ketones, as well as mixtures of two or more such ketones. Most preferred is diethyl ketone (3pentanone). The arylation reaction inherently tends to be an exothermic reaction, and the use of diluents having a dielectric constant in the range of about 10 to about 30 (as measured at 20° to 25° C.), such as a ketone meeting this qualification provides a readily controllable reaction.

The palladium catalyst system used is formed from (i) palladium and/or at least one compound of palladium in which the palladium has a valence of zero, 1 or 2, and (ii) a tertiary phosphine ligand having at least one aryl group in the molecule. The solvent/diluent used preferably has at least a measurable polarity at a temperature in the range of 20° to 25° C., and yet is free of functionality that would prevent or materially impair, inhibit or otherwise materially interfere with the arylation reaction.

In forming the palladium catalyst system the use of salts of palladium is preferable because catalyst compositions formed from palladium salts appear to have greater activity than those made from palladium metal itself. Of the salts, palladium(II) salts such as the Pd(II) halides (chloride, bromide, iodide) and Pd(II) carboxylates (e.g., acetate, propionate, etc.) are most preferred. The phosphine ligand has the formula $R^1R^2R^3P$ where $R^1$, $R^2$, and $R^3$ are the same or different and are selected from alkyl, cycloalkyl, aryl, heteroaryl, and aralkyl, and where at least one of $R^1$, $R^2$, and $R^3$ is aryl. Preferably at least one of $R^1$, $R^2$, and $R^3$ is aryl and at least one of $R^1$, $R^2$, and $R^3$ is cycloalkyl.

A highly preferred type of tertiary phosphine ligand used is one or more tertiary phosphines of the formula

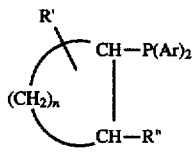

where R' and R" are the same or different and are individually hydrogen, alkyl, aryl, Ar is phenyl, naphthyl, substituted phenyl or substituted naphthyl and n is an integer from 3 to 6. Preferably, R' and R" are the same or different and are $C_1$ are $C_6$ alkyl, Ar is phenyl or naphthyl and n is 3 or 4. Most preferrably, R' is methyl or ethyl, R" is $C_3$ to $C_6$ branched alkyl, Ar is phenol and n is 4. Especially preferred as the phosphine ligand is neomenthyldiphenylphosphine.

Active catalytic species are preferably formed in situ by the addition to the reaction mixture of the foregoing individual components. However the catalyst can be preformed externally to the reaction mixture and charged to the reactor as a preformed catalyst composition.

One or more secondary or tertiary amines are included in the reaction mixture to serve as a hydrogen halide acceptor. Such amines are used in at least a stoichiometric amount relative to the aryl halide and/or substituted aryl halide being used. Triethylamine is a preferred amine for this use.

Liquid media formed from diethyl ketone and acetonitrile (e.g. in a weight ratio in the range of 1:9 to 4:1, and more preferably in the range of 1:3 to 3:1) plus triethylamine, or from diethyl ketone and N,N-demethylformamide (e.g., in a weight ratio in the range of 1:9 to 9:1) plus triethylamine are typical desirable liquid media for use in the arylation reaction. Liquid media formed from diethyl ketone and triethylamine or from methyl isobutyl ketone and triethylamine are particularly preferred.

Desirably, a small reaction-accelerating amount of water is included or present in the reaction mixture, as described in commonly-owned U.S. application Ser. No. 08/780,310, filed Jan. 8, 1997, all disclosure of which is incorporated herein. This amount is typically in the range of about 0.5 to about 5 wt % of the total weight of the entire reaction mixture. Within the range of about 0.5 to 5 weight percent water there is often an optimum amount of water which gives the highest or peak reaction rate which falls off if more or less water is used. This optimum amount of water may vary depending upon the identity and proportions of the ingredients used in forming the reaction mixture. Thus in any given situation it may be desirable to perform a few preliminary experiments with the particular reaction to be conducted, wherein the amount of water is varied within the range of about 0.5 to about 5 wt % to locate the optimum rate-enhancing amount of water in the mixture. Preferably, the amount of water used will be insufficient to form a second liquid phase (i.e., a separate water layer) in a mixture consisting of (i) the amount of the liquid organic solvent/ diluent(s) selected for use, (ii) the selected amount of the liquid secondary and/or tertiary amine(s) selected for use, and (iii) the selected amount of water, when such mixture is agitated for 10 minutes at 25° C. and allowed to stand for 15 minutes at the same temperature. Thus when conducting the process on a large scale with recycle of solvent(s) and amine, the amount of water carried over from product workup should be monitored and/or controlled such that the water content of the reaction mixture remains at or below about 5 wt % of the total weight thereof. Conversely if the amount of recycled water is insufficient to maintain the desired water content in the reaction mixture, additional water should be added to bring the water content up to the desired amount within the foregoing range. Preferably the arylation reaction mixtures have a water content in the range of about 1 to about 3.5 weight percent.

The ratio of aryl halide to secondary alkenol is not critical, as the reaction involves one mole of each reactant. Thus if the molar ratio of either reactant materially exceeds the other, the reactant present in the smaller molar quantity becomes the limiting reactant. Therefore, typically about 0.8 to about 1 mole of aryl halide are used per mole of secondary alkenol. The mole ratio of aryl halide:Pd:ligand used will generally be a suitable ratio within the range of 200–20,000:1:1–20, respectively. The conduct of the palladium-catalyzed arylation reaction in the preferred manner involves proportions of about 0.90 to about 0.95 mole of aryl halide per mole of secondary alkenol, a ratio of about 0.0005 to about 0.005 mole of palladium or palladium compound per mole of aryl halide, and a mole ratio of about 0.5 to about 10 moles of tertiary phosphine ligand per mole of palladium or palladium compound.

Temperatures of the arylation reaction are quite modest, varying from about 25° C. to 200° C. (preferably 60° C. to 150° C.). Typically the reaction is conducted at atmospheric or autogenous pressures. Reaction times are typically in the range of 12 to 48 hours.

The allylic aralkenyl secondary alcohol can be recovered from the reaction mixture and then subjected to the transformation process, or alternatively, the iron polycarbonyl can be added to the reaction mixture from the arylation reaction followed by conduct of the transformation process. Such a procedure is often termed a "one-pot reaction".

The following examples are given to illustrate this invention and are not intended as a limitation thereof. Unless otherwise specified all percentages given therein are by weight. The following designations are used in the examples:

BMN is 2-bromo-6-methoxynaphthalene.

TEA is triethylamine.

NMDP is neomenthyldiphenylphosphine.

ACN is acetonitrile.

Example I illustrates a two-stage procedure. A one-pot reaction is illustrated by Example II.

EXAMPLE I

First Stage

BMN (20.0 g; 84.4 mmol) was added to a 250 mL 3-neck flask and transferred into a drybox. PdCl$_2$ (133 mg) and NMDP (1.13 g) were added, and the flask (with condenser attached) placed in a hood under nitrogen over-pressure. ACN (80 mL), TEA (35 mL), and 3-buten-2-ol (6.5 g; 90 mmol) were added, and the reaction mixture heated to a vigorous reflux. After 41 hours, the mixture was cooled to ambient room temperature, quenched with 0.2M HCl (100 mL), and diethyl ether (100 mL) was added. The layers were separated, the aqueous layer extracted with ether (75 mL), and the combined organic layers were dried (Na$_2$SO$_4$), filtered, and concentrated affording 20.25 g (100%) of an off-white solid. GC, GC/MS, and $^1$H NMR showed the product to be a mixture of 43% 4-(6'-methoxy-2'-naphthyl) -butan-2-one, 46% 4-(6'-methoxy-2'-naphthyl)-but-3-en-2-ol, and 11% other substances (some of which were isomers of the initial allylic alcohol).

Second Stage

A sample (0.5 g) of the ketone/alcohol product mixture produced in the first stage was dissolved in benzene (40 mL). Fe$_3$(CO)$_{12}$ (0.20 g) was added and the mixture heated to 70° C. for 45 minutes. Analysis by GC and $^1$H NMR showed that all of the 4-(6'-methoxy-2'-naphthyl)-but-3-en-2-ol had been converted to 4-(6'-methoxy-2'-naphthyl) butan-2-one.

EXAMPLE II

BMN (20.0 g; 84.4 mmol) was added to a 250 mL 3-neck flask. PdCl$_2$ (133 mg) and NMDP (1.13 g) were added in a drybox, and the flask (with condenser attached) placed under nitrogen in a hood. ACN (80 mL), TEA (35 mL), and 3-buten-2-ol (6.5 g; 90 mmol) were added, and the reaction mixture heated to a vigorous reflux. After 26 hours, the mixture was cooled to about 40° C., Fe$_3$(CO)$_{12}$ (5.0 g) was added directly to the mixture in the same reactor, and the mixture was heated back to reflux. After 3.5 hours, the reaction mixture was cooled to 0° C., 1N HCl (80 mL) was added, and the mixture was stirred overnight. Ether (100 mL) was added, the layers were separated, the aqueous layer was extracted with ether (30 mL), and the combined organic layers were dried (Na$_2$SO$_4$), filtered, and concentrated. GC analysis showed that conversion to a 53 to 25 ratio of 4-(6'-methoxy-2'-naphthyl)-butan-2-one to 4-(6'-methoxy-2'-naphthyl-but-3-en-2-ol had been achieved.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Without limiting the generality of the foregoing, as an illustrative example, where a claim specifies that a catalyst is a palladium compound in combination with a tertiary phosphine ligand, this phraseology refers to the makeup of the individual substances before they are combined and/or mixed separately or concurrently with one or more other materials, and in addition, at the time the catalyst is actually performing its catalytic function it need not have its original makeup—instead whatever transformations, if any, that occur in situ as the catalytic reaction is conducted is what the claim is intended to cover. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for forming an alkyl aralkyl ketone from an aralkenyl secondary alcohol having an allylic double bond relative to the hydroxycarbinyl group, and having the allylic double bond disposed between the aryl moiety and the hydroxycarbinyl group, which process comprises heating said alcohol in a suitably inert organic liquid medium to which a catalytic quantity of an iron polycarbonyl has been added.

2. A process according to claim 1 wherein said alcohol is depicted by the formula

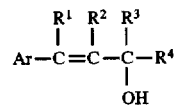

where each of R$^1$ and R$^2$ is, independently, a hydrogen atom, or an alkyl group containing 1 to 3 carbon atoms; R$^3$ is a hydrogen atom or a methyl group; R$^4$ is an alkyl group containing 1 to 4 carbon atoms; and Ar is a 2-naphthyl group having a substituent in the 6-position.

3. A process according to claim 1 wherein said alcohol is 4-(6'-methoxy-2'-naphthyl)-but-3-en-2-ol.

4. A process according to claim 1 wherein said iron polycarbonyl as it is being added to said medium is Fe$_3$(CO)$_{12}$.

5. A process according to claim 1 wherein said iron polycarbonyl as it is being added to said medium is Fe(CO)$_5$.

6. A process which comprises heating a liquid phase mixture formed at least from (i) one or more aralkenyl secondary alcohols having an allylic double bond relative to the hydroxycarbinyl group, and having the allylic double bond disposed between the aryl moiety and the hydroxycarbinyl group, and (ii) at least one iron polycarbonyl, said heating being conducted at one or more temperatures and for a period of time such that transformation of at least a portion of said one or more aralkenyl secondary alcohols to one or more alkyl aralkyl ketones occurs.

7. A process according to claim 6 wherein said liquid phase mixture is additionally formed from one or more alkyl aralkyl ketones corresponding to the alkyl aralkyl ketone to be formed in the process.

8. A process according to claim 6 wherein said liquid phase mixture is additionally formed from at least one liquid organic solvent that does not prevent said transformation from occurring.

9. A process according to claim 6 wherein said one or more alcohols is/are depicted by the formula

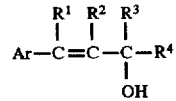

where each of R$^1$ and R$^2$ is, independently, a hydrogen atom, or an alkyl group containing 1 to 3 carbon atoms; R$^3$ is a hydrogen atom or a methyl group; R$^4$ is an alkyl group containing 1 to 4 carbon atoms; and Ar is a 2-naphthyl group having a substituent in the 6-position.

10. A process according to claim 9 wherein said iron polycarbonyl as it is being used in forming said liquid phase mixture is $Fe_3(CO)_{12}$.

11. A process according to claim 9 wherein said iron polycarbonyl as it is being used in forming said liquid phase mixture is $Fe(CO)_5$.

12. A process according to claim 6 wherein said alcohol is 4-(6'-methoxy-2'-naphthyl)-but-3-en-2-ol.

13. A process according to claim 12 wherein said iron polycarbonyl as it is being used in forming said liquid phase mixture is $Fe_3(CO)_{12}$.

14. A process according to claim 12 wherein said iron polycarbonyl as it is being used in forming said liquid phase mixture is $Fe(CO)_5$.

15. A process which comprises (a) forming allylic secondary arylalkenol by palladium-catalyzed arylation of an allylic secondary alkenol with an aryl halide, and (b) heating a liquid phase mixture formed from at least the following ingredients or components: (i) at least a portion of the allylic secondary arylalkenol formed in (a) and (ii) at least one iron polycarbonyl, such that alkyl aralkyl ketone is produced having the same skeletal configuration as the aralkenol but without the double bond.

16. A process according to claim 15 wherein at least a portion of at least the allylic secondary arylalkenol formed in (a) is recovered from the reaction mixture formed in (a) and is then subjected to (b) while dissolved in a fresh liquid organic solvent that does not prevent said alkyl aralkyl ketone from being produced.

17. A process according to claim 15 wherein the recovered portion of the allylic secondary arylalkenol formed in (a) is in admixture with the corresponding alkyl aralkyl ketone, and it is this mixture that is used in forming the liquid phase mixture that is heated in (b).

18. A process according to claim 15 wherein the iron polycarbonyl is added to the reaction mixture formed in (a) without recovering the allylic secondary arylalkenol therefrom.

19. A process according to claim 18 conducted as a one-pot reaction.

* * * * *

UNITED STATES PATENT AND TRADEMARK OFFICE
CERTIFICATE OF CORRECTION

PATENT NO.  : 5,741,938
DATED       : April 21, 1998
INVENTOR(S) : Stephen E. Belmont It is certified that error appears in the above-identified patent and that said Letters Patent is hereby corrected as shown below:

Cover Page, Item [54], and in column 1, lines 1-3, title reads
"PRODUCTION OF ALKYL ARALKYL KEONES FROM ALLYLIC-ARALKENYL SECONDARY ALCOHOLS"

and should read

--PRODUCTION OF ALKYL ARALKYL KETONES FROM ALLYLIC-ARALKENYL SECONDARY ALCOHOLS--.

Signed and Sealed this

Twenty-seventh Day of July, 1999

Attest:

Attesting Officer

Q. TODD DICKINSON

Acting Commissioner of Patents and Trademarks